United States Patent [19]

L'Esperance, Jr.

[11] Patent Number: 5,300,020

[45] Date of Patent: Apr. 5, 1994

[54] SURGICALLY IMPLANTABLE DEVICE FOR GLAUCOMA RELIEF

[75] Inventor: Francis A. L'Esperance, Jr., Englewood, N.J.

[73] Assignee: Medflex Corporation, Durham, N.C.

[21] Appl. No.: 954,653

[22] Filed: Sep. 30, 1992

Related U.S. Application Data

[63] Continuation of Ser. No. 708,764, May 31, 1991, abandoned.

[51] Int. Cl.⁵ .............................................. A61M 5/00
[52] U.S. Cl. .......................................... 604/9; 623/4
[58] Field of Search .................. 604/8, 9, 175, 264; 623/4

[56] References Cited

U.S. PATENT DOCUMENTS

| | | | |
|---|---|---|---|
| 3,949,750 | 4/1976 | Freeman | 604/294 |
| 3,960,150 | 6/1976 | Hussain et al. | 604/294 |
| 4,457,757 | 7/1984 | Molteno | 604/294 |
| 4,722,724 | 2/1988 | Shocket | 604/8 |
| 4,787,885 | 11/1988 | Binder | 604/8 |
| 4,915,684 | 4/1990 | MacKee et al. | 604/8 |
| 4,936,825 | 6/1990 | Ungerleider | 604/8 |
| 4,946,436 | 8/1990 | Smith | 623/4 |

Primary Examiner—Jerome L. Kruter
Attorney, Agent, or Firm—Hopgood, Calimafde, Kalil, Blaustein & Judlowe

[57] ABSTRACT

The invention contemplates a surgically implantable device for controlled drainage flow of aqueous fluid from the anterior chamber of the eye into nearby subconjunctival space, all in relief of a glaucomatous condition of excessive pressure within the eye. The device includes provision for so controlling the rate of aqueous flow as to assure against anterior-chamber collapse, thus avoiding irreparable damage which might otherwise result to the corneal endothelium, to the iris, or to the lens of the eye.

17 Claims, 3 Drawing Sheets

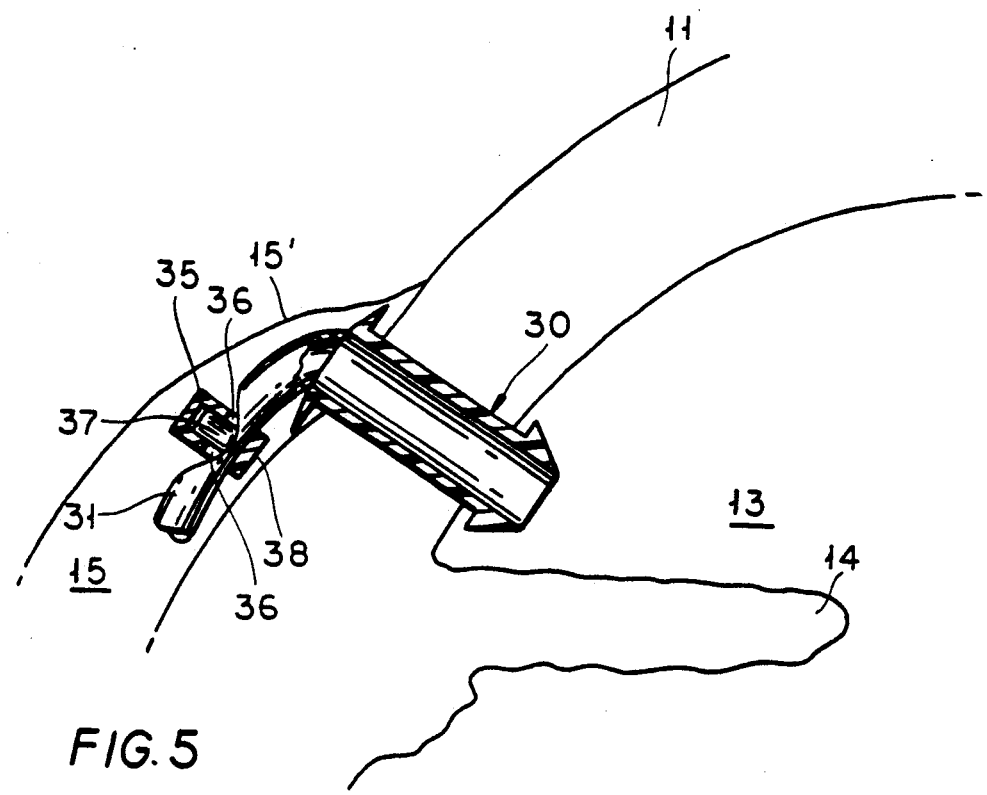
FIG. 5
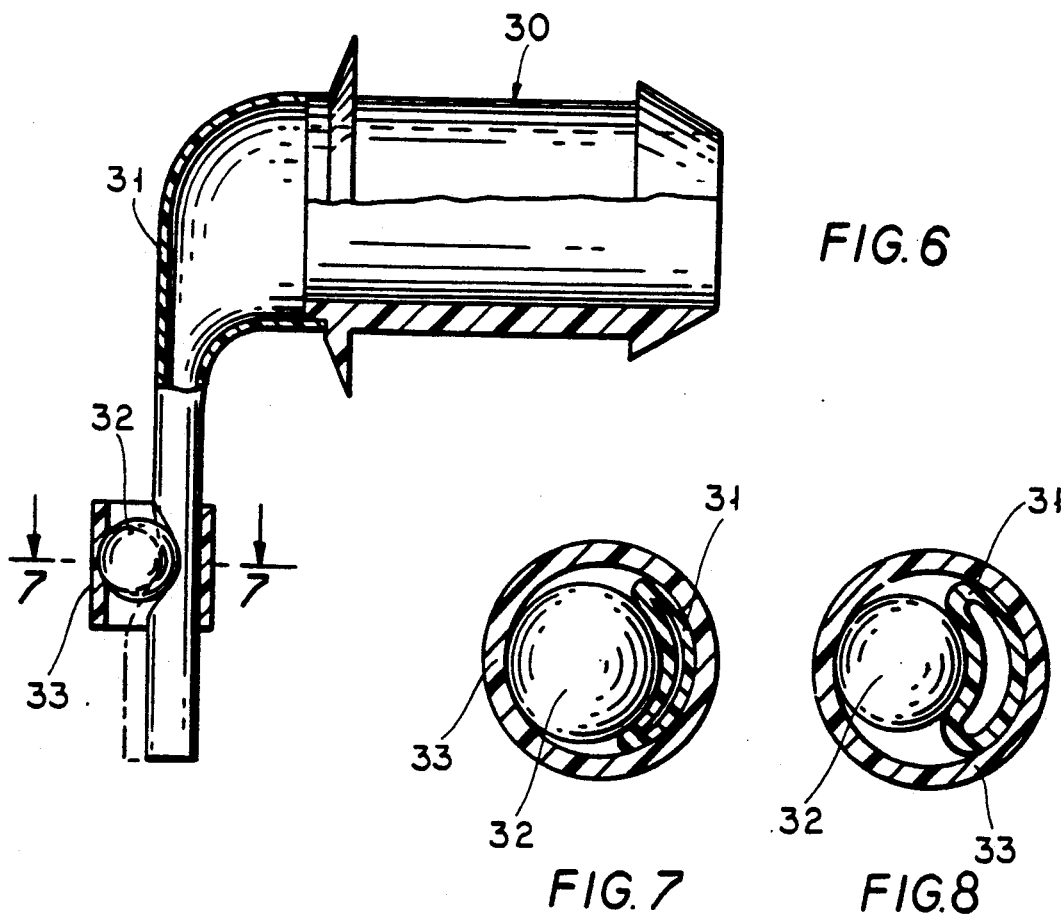
FIG. 6
FIG. 7
FIG. 8

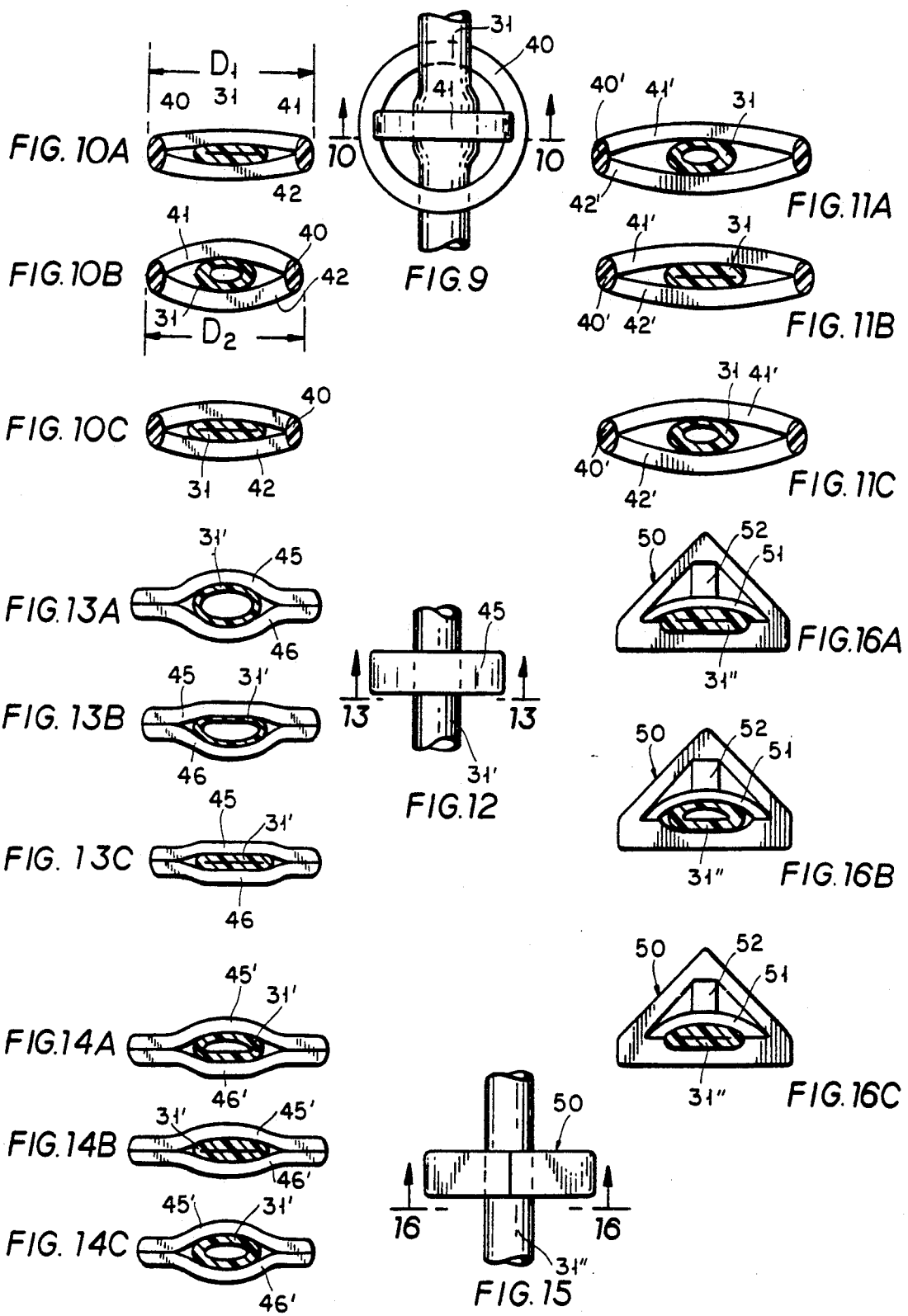

SURGICALLY IMPLANTABLE DEVICE FOR GLAUCOMA RELIEF

RELATED CASE

This application is a continuation of original application Ser. No. 07/708,764, filed May 31, 1991, now abandoned.

FIELD OF THE INVENTION

Background of the Invention

The invention relates to surgically implantable means for use in aid of an operative procedure in relief of a glaucoma condition of an eye.

Glaucoma is a state of elevated pressure within an eyeball. If unrelieved, the condition will result in damage to the optic nerve and retina, and gradual loss of vision.

Related Art

It is a known treatment for glaucoma that a canal be surgically developed through the sclera to the base of the anterior chamber, i.e., near the location of iris juncture to the sclera, whereby a channel of aqueous drainage is established to the subconjunctival space. But unless extreme care is taken, aqueous drainage can be so rapid and to such an extent as to cause anterior-chamber collapse, with irreparable damage to the corneal endothelium, to the iris, or to the lens of the eye.

SUMMARY OF THE INVENTION

It is an object of the invention to provide a surgically implantable device for controlled drainage flow of aqueous fluid from the anterior chamber of an eye into nearby subconjunctival space, such that the flow will proceed slowly enough to avoid possible anterior-chamber collapse, with resulting damage to the corneal endothelium or to other parts of the eye.

It is a specific object to provide means meeting the above object and permitting surgical implantation with minimum loss of aqueous fluid.

Still another specific object is to provide such a device with controllable means whereby drainage flow can be either totally foreclosed or held to a tolerable minimum until the surgeon is satisfied that conditions are favorable for a controlled increase in flow accommodation.

A further specific object is to provide improved means to control relief of anterior chamber and intraocular pressure with assurance of maintaining anterior-chamber depth until the related conjunctival incision has healed adequately.

The invention achieves these objects and provides certain further features in a surgically implantable device in the form of a tubular element having spaced tissue-engaging formations to retain itself by limited engagement with inner and outer adjacent surfaces of the cornea at the location of a hole through the cornea and adjacent sclera. The tubular element contains or is otherwise associated with means for so controlling the rate of aqueous flow as to assure against anterior-chamber collapse, thus avoiding irreparable damage which might otherwise result to the corneal endothelium, to the iris, or to the lens of the eye. Various embodiments are described.

BRIEF DESCRIPTION OF THE DRAWINGS

Preferred embodiments of the invention will be described, in conjunction with the accompanying drawings, in which:

FIG. 5 is another view similar to FIG. 1, showing another modification;

FIG. 6 is a view similar to FIG. 2, showing the device of FIG. 5;

FIG. 7 is a sectional view taken at 7—7 in FIG. 6 to show a control element in one operative control state;

FIG. 8 is a similar sectional view at 7—7 in FIG. 6 to show another operative control state;

FIG. 9 is an enlarged fragmentary view of a first category of control-element modification from the embodiment of FIGS. 7 and 8;

FIGS. 10a, 10b, and 10c are a series of three diagrams to show separate control states of the control element of FIG. 9, all as viewed in the section plane 10—10 of FIG. 9;

FIGS. 11a, 11b, and 11c are another series of three diagrams to show separate control states of another control element as in FIG. 9, all as viewed in the section plane 10—10 of FIG. 9;

FIG. 12 is another enlarged fragmentary view to show a second category of control-element modification from the embodiments of FIGS. 7, 8 and 9;

FIGS. 13a, 13b, and 13c are a series of three diagrams to show separate control states of the control element of FIG. 12, all as viewed in the section plane 13—13 of FIG. 12; FIG. 12;

FIGS. 14a, 14b, and 14c are another series of three diagrams to show separate control states of another control element as in FIG. 12, all as viewed in the section plane 13—13 of FIG. 12;

FIG. 15 is still another enlarged fragmentary view to show a third category of control-element modification; and FIGS. 16a, 16b and 16c are a series of three diagrams to show control states of the control element of FIG. 15.

DESCRIPTION OF THE PREFERRED EMBODIMENTS

Figure 1:
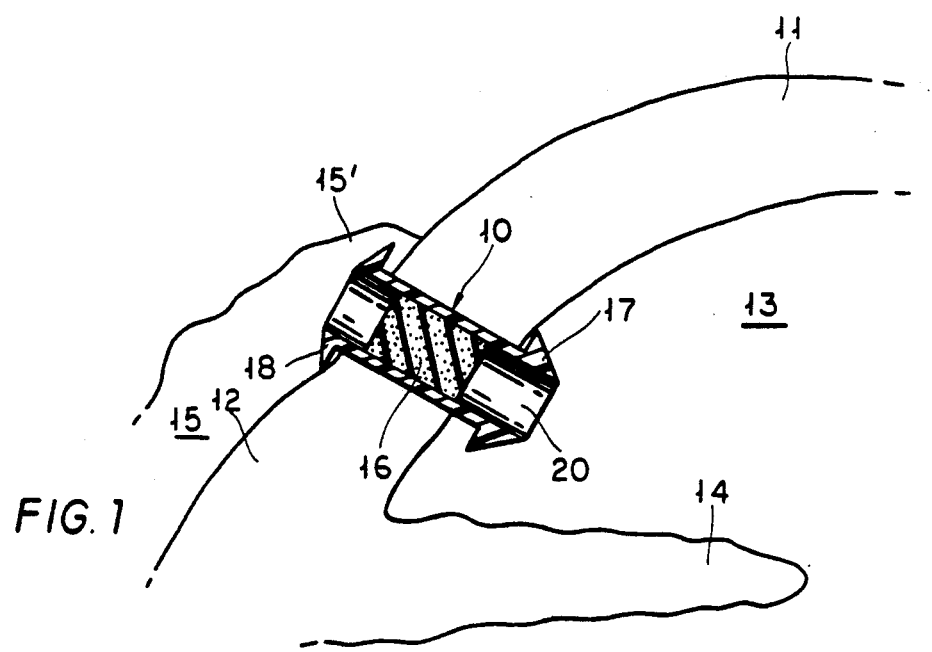
FIG. 1 is an enlarged fragmentary sectional view of a glaucomatous eye that has been fitted with a surgical implant device of the invention, the section being longitudinal along the axis of the implant device.

In FIG. 1, a glaucomatous eye is seen following surgery wherein a tubular drainage device 10 has been inserted in a hole through the cornea 11 and adjacent sclera 12, to provide controlled flow of aqueous fluid from a corner of the anterior chamber 13 (adjacent nearby iris tissue 14) and into subconjunctival space 15. The making of such a hole is a well-understood surgical procedure, involving one of several alternative techniques, as by direct laser sclerostomy (e.g., a holmium laser), trephine (e.g., using an Elliot trephine), or transconjunctival laser sclerostomy which is transmitted through the conjunctival tissue 15' on the way to and through the cornea-scleral tissue. In adopting such drilling techniques, the ever-present danger is the relatively sudden release of aqueous flow without any means to control or curtail the flow.

In accordance with a feature of the invention, the drainage device 10, which is surgically implanted immediately after drilling the described hole, is insertionally implanted in the hole, and this device 10 incorporates its own means 16 of flow control. The device 10 is better seen in FIGS. 2 and 3 to be a small cylindrical tube with radially outward retaining-flange formations 17–18 at its respective ends. Both flange formations are frusto-conical, the lead-end flange 17 having a gentle conical apex-angle slope for ease of insertion, and the rear-end flange 18 being much more steeply sloped, to reduce as much as possible the extent to which an inserted device 10 projects into or interferes with flow into subconjunctival space.

As shown, the device 10 has a smooth cylindrical bore 20 which extends the full length of device 10, and the flow-control means 16 is a plug of absorbable material which maintains anterior-chamber pressure initially, thus giving time (in the order of several days) for a degree of healing repair of the conjunctiva, where the initial incision occurred. Later, when aqueous fluid has been fully absorbed into means 16, a path of relatively slow drainage flow will have established itself, conducting aqueous flow into the subconjunctival space, until an equilibrium of pressures is developed, as between the anterior chamber and the subconjunctival space. Meanwhile pressure release in the anterior chamber has been so slow as to assure against collapse of the cornea and resulting damage to any part of the eye, yet sufficient to lower the intraocular pressure.

More specifically with regard to device 10, the length L between outer flanges 17–18 is suitably about 2-mm, i.e., in the range 1.5 to 2.5-mm, and the bore diameter D is suitably in the range 1.0 to 2-mm. The body of device 10 is of relatively soft, resilient inert and biocompatible material, such as silicone rubber. The plug 16 is of biomedically compatible absorbing material (e.g., a solidified fibrin material having porous properties), and its length will predictably delay flow into subconjunctival space for a matter of days, thereby maintaining anterior-chamber depth while allowing conjunctival surgery a sufficient healing opportunity; illustratively, a 1-mm long plug 16 having slight interference fit (for retention) in a 1.5-mm long bore in device 10 and formed of fibrin material will provide the desired flow delay for 3 to 7 days.

Stated in pressure terms, a glaucoma condition is defined by an anterior-chamber pressure of at least 21-mm Hg above ambient, while in a normal eye, such pressure is in the range of 16 to 18-mm Hg. But glaucomous pressure can be much greater than the 21-mm Hg threshold, rising in most cases to 24 or 25-mm Hg and, in severe cases, to as much as 30–40-mm Hg. And if precautions are not taken to prevent corneal collapse, drops of pressure to as low as 0–2-mm Hg can occur. The device 10 with its time delay of anterior-chamber pressure release through controlled aqueous-drainage flow into subconjunctival space assures against such a disastrous drop in pressure, yet relieves the glaucomatous condition by lowering the intraocular pressure to a normal range.

Figures 2, 3:
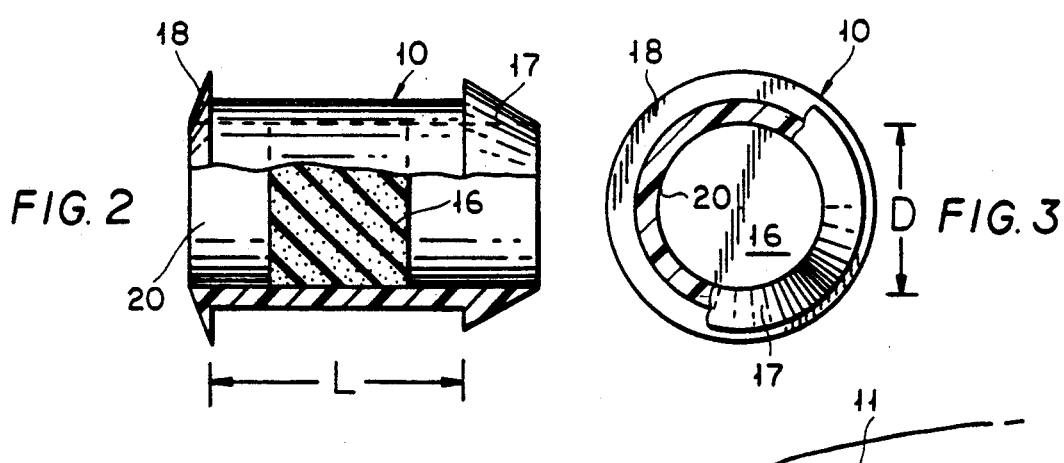
FIG. 2 is a side elevation, partly in section, for the implant device of FIG. 1.
FIG. 3 is a right-end view of the device of FIGS. 1 and 2.
Figure 4:
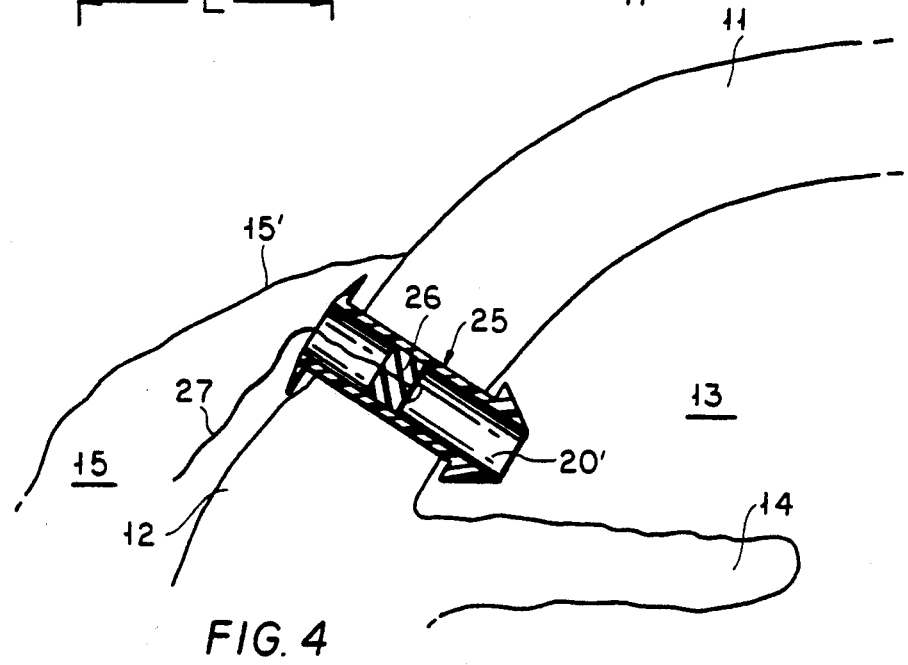
FIG. 4 is a view similar to FIG. 1, showing a modified implant device.

In the arrangement of FIG. 4, a surgically implanted flow-control device 25 may be as described at 10 in FIGS. 1 to 3, except that the plug 26 in the bore of device 25 is relatively non-absorbent, affording the surgeon the option of such extended time after making the implantation, as he deems necessary to the conjunctival healing process. The plug 26 incorporates a pull-cord 27, e.g., of suture material, which is shown draped down into subconjunctival space, but which can be rendered accessible where and as the surgeon may decide; he need only pull the cord 27 to dislodge plug 26 from the bore of device 25, when he decides that the time is right. The removed plug and its cord may be of material that is ultimately soluble in body fluids.

In the arrangement of FIG. 5, a surgically implanted device 30 may be generally as described for devices 10 and 25, except that device 30 includes a flexible drainage tube 31 which not only bends for aqueous-flow discharge directly into subconjunctival space, but which also incorporates its own time-delay valve-opening structure, one embodiment of which is illustratively shown in detail in FIGS. 6 to 8.

In FIGS. 6 to 8, a ball 32 of biocompatible absorbable material (e.g., collagen) is the means of applying a valve-closing squeeze on tube 31, it being noted than an annular body 33 has a bore which is threaded by tube 31, and that a local indentation in the bore locates ball 32 in its initially installed relation of valve-closing action on tube 31. This is the condition depicted on an enlarged scale in FIG. 7. As body fluids gradually dissolve the material of ball 32, the valve-closing force of the ball is reduced, to create a valve-opening condition, as depicted in FIG. 8.

Alternatively, the valve-opening structure of FIG. 5 may be understood to be a rigid enclosure body 35 having opposed ported openings 36 for transversely threaded accommodation of tube 31, and a valve member 37 is captive within the upper cavity portion of body 35; valve member 37 may be cylindrical, with a spherically rounded lower end, and of photon-sensitive shrinkable plastic material, initially formed in its longitudinally elongate condition so as to assure full-closure valve action wherein tube 31 is compressed by valve member 37 against the bottom-closure wall 38 of body 35. When the surgeon wishes to release anterior-chamber pressure, he need only apply a transient exposure of photon energy, as by localized visible or infrared exposure to the conjunctival region of adjacency to the valve body and its retained member 37. Initial aqueous-drainage flow is immediately recognized by an initial drop in anterior-chamber pressure, which can be monitored by conventional means. And, of course, the rate of anterior-chamber pressure reduction will be determined by the surgeon, i.e., by how great and of what duration is the coherent or incoherent light exposure to the photon-sensitive valve member 37.

The remaining figures of the drawings relate to various alternatives and modifications of valve-control structure forming part of the aqueous-drainage system of the invention. These may be generally referred to as structures involving polymer components which either inherently or by reason of special compounding (as with different chromophores) are selectively shrinkable or stretchable to effect opening and/or closure operation of means for effecting a variable constricting squeeze on tube 31.

The arrangement of FIGS. 9 and 10 comprises three parts, each of which is differently compounded for selective shrink response to a different irradiating wavelength. The basic frame part 40 is a circular ring, shown with elliptical section. The tube 31 passes through ring 40, and in its initial condition (FIG. 10a) tube 31 is squeezed to closed condition by opposed arms 41, 42 which are connected (as by local fusing) to diametrically opposite regions of ring 40. The squeezing force of arms 41, 42 on tube 31 and the thickness of the squeezed tube necessarily involve outward bowing of these arms at the location of squeeze action. Each of the parts 40, 41, 42 is a different polymer product, in initially stretched condition, and having its own property of shrink response to a different irradiating wavelength. Thus, the polymer of ring 40 may, by reason of compounding with a first chromophore, be organized in such a way that ring 40 will shrink only when exposed to a blue wavelength; while the polymer of arm 41 may be organized such that arm 41 will shrink only when exposed to a yellow wavelength, and the polymer of arm 42 may be organized such that arm 42 will shrink only when exposed to a red or infrared wavelength.

Thus, it will be understood that in the configuration of FIGS. 9 and 10a, each of the elements 40, 41, 42 is responsive to a different irradiating wavelength, and that each of the three involved polymers will have been stretched prior to cooling, so that in response to the wavelength unique to the particular polymer, the involved element or elements will be actuated to return to their prestretched state. Since all elements 40, 41, 42 are in prestretched state, ring 40 will initially be of maximum outer diameter $D_1$, but upon irradiation at the shrink-response wavelength unique to the polymer of ring 40, the latter will shrink, to the exclusion of any change of state of either of arms 41, 42. FIG. 10b illustrates such shrinkage of ring 40, from its initial diameter $D_1$, to its reduced diameter $D_2$; FIG. 10b also illustrates that because neither of the arms 41, 42 has been affected by the irradiation, the shrinkage of ring 40 has forced arms 41, 42 to compliantly deform with an elastic increase in their outward bowing, thereby releasing their clamp action on tube 31 and allowing tube 31 to open for an aqueous-drainage flow.

Now if for any reason, the surgeon should decide that the aqueous flow (permitted by the FIG. 10b condition) should be reduced or brought to a halt, exposure of the device to irradiation at the response wavelength of arm 41 will not only induce arm 41 to shrink but will also reduce its compliantly stressed bow, thereby increasing the squeeze on tube 31 and materially reducing the permitted aqueous outflow. On the other hand, if the irradiation includes the unique response wavelengths of both arms 41, 42, then both arms will shrink, their bowing will reduce, and clamp action will effectively close the lumen of the valve, as depicted in FIG. 10c.

The device of FIGS. 9 and 10a may be said to be of "closed/open/closed" variety, in recognition of the succession of operations depicted in FIGS. 10a, b, c. The same general configuration of FIG. 9 may also serve to provide a valve action of "open/closed/open" variety, as depicted in the succession of FIGS. 11a, b, c.

In FIG. 11a, parts corresponding to those of FIG. 10a are given the same reference numbers, but with primed notation, involving the three parts 40', 41', 42' and their selective action on tube 31. The parts 40', 41', 42' are so structured in their stretched condition that tube 31 is open, as depicted in FIG. 11a. Thereafter, by irradiation at the response wavelength of arm 41', or by irradiation at the response wavelength of arm 42', or at both of these wavelengths, tube 31 is either partially closed (e.g., by shrinkage on one to the exclusion of the other arm), or it is fully closed (by shrinkage of both arms), as depicted in FIG. 11b. Subsequent irradiation at the response wavelength of ring 40' is operative to constrict ring 40', thereby forcing compliant greater bowing of arms 41', 42', with accompanying reopening of the lumen of the valve, as seen in FIG. 11c.

FIGS. 13 and 14 depict different kinds of valve action achievable on a squeezable tube 31', using a two-element actuator which has the plan view appearance of FIG. 12. The two parts are initially stretched, shrinkable, polymer arms 45, 46, of like appearance but differently compounded, for individual unique response to different irradiating wavelengths. In FIG. 13, the arms 45, 46 connected at their ends, and are structured in their stretched condition with sufficient outward bowing to provide a maximum opening of tube 31', as seen in FIG. 13a. Irradiation at only the response wavelength of one arm (45) will effect a shrinkage and noticeable flattening of the involved arm (45), with resultant reduction of the valve passage of tube 31', as seen in FIG. 13b. Later, irradiation at the response wavelength of the other arm (46) will effect a corresponding shrinkage and flattening of the other arm (46), with resulting closure of the lumen of tube 31', as shown in FIG. 13c.

FIG. 14 illustrates the ability of a two-part control means, having the same plan as in FIG. 12, to provide a selectively operable "open-close-open" action on the flexible tube 31'. Initially, the arms 45', 46' of FIG. 14 are constructed in their stretched condition to provide an open condition of tube 31', as shown in FIG. 14a; this resembles the condition shown at FIG. 13b, except that in its stretched condition per FIG. 14a, the bulge in lower arm 46' is initially relatively shallow, as compared with the greater bulge in upper arm 45'. In this configuration, the lumen of tube 31' is more flat in adjacency to arm 46', and it is more rounded in adjacency to arm 45'. Upon irradiation at the shrink-response wavelength of the polymer material of arm 45', the involved shrinkage of arm 45' reduces its bulge and completes closure of the lumen of tube 31', as seen in FIG. 14b. And later, upon irradiation at the shrink-response wavelength of arm 46', its shrinkage applies longitudinal compression to arm 45' which can react only, by adopting a more bulging contour as seen in FIG. 14c, with a resulting reopening of tube 31'.

In the configuration of FIGS. 15 and 16, a rigid open triangular frame 50 is internally contoured along one of its sides, to accept and determine a locally flattened lower half of a flexible tube 31". Use of the word "rigid" is meant to indicate that frame 50 is essentially non-shrinkable and that it is not responsive to any type of irradiation. Shrinkably active elements comprise a bowed transverse arm 51 which straddles tube 31" and which is initially contoured to confine, and effectively flatten, the upper half of tube 31", to the point of closing the lumen of tube 31", as seen in FIG. 16a. This flattening action is aided by compressive force applied to the center of arm 51 by a longitudinally stretched second element 52, it being noted that the upper and lower ends of element 52 are fused or otherwise attached (a) to a flat inside the apex of the triangular frame 50, and (b) to the midpoint of the bowed arch of element 51.

In contrast to all previously described valve-actuating means for selectively opening and/or closing a flexible tube, such as tube 31", the shrinkably active elements 51, 52 of FIGS. 15 and 16 each have separate responses to each of two different irradiating wavelengths. The polymer material of element 51 includes a first chromophore responsive to a first irradiation wavelength to induce shrinkage of element 51; this polymer material also includes a second chromophore responsive to a second irradiation wavelength to induce heating to the point of rendering element 51 pliable and therefore stretchable. Similarly, the polymer material of element 52 includes a third chromophore responsive to a third irradiation wavelength to induce shrinkage of element 52', and the polymer material of element 52 also includes a fourth chromophore responsive to a fourth irradiation wavelength to induce heating to the point of rendering element 52 pliable and therefore stretchable. For any single valve actuation, e.g., for a valve (tube 31") opening, one of the shrinkably active elements is initially stretched and therefore is shrinkable, while the other shrinkably active element is in a contracted state and therefore is heat-softenable to permit its stretching. More specifically, starting with the valve (tube 31") closed condition of FIG. 16a, concurrent irradiation at the above-noted second and third wavelengths will induce shrinkage of element 52 and softening-plus-stretch of element 51, in the course of proceeding in the valve-opening direction of FIG. 16b. And to return from the valve-open condition of FIG. 16b, to or in the direction of the valve-closure condition of either FIG. 16c or FIG. 16a, concurrent irradiation at the above-noted first and fourth wavelengths will induce shrinkage and flattening of element 51 and softening-plus-stretch of element 52. The two different actions can be repeatedly reversed and run to the extent desired, resulting in a constantly titratable kind of valve system, depending upon the particular combination of irradiating wavelengths used to activate element 51 or element 52 for closing or opening the valve (tube 31"), as the case may be.

It will be understood that the various valve-control structures described herein are applicable to situations and uses other than aqueous drainage for relief of a glaucomatous pressure condition. In particular, all implantable devices are to be understood as being made from biocompatible materials, and tubular bodies 25, 31, 31', 31" are suitably made of inert, flexible, and resilient material such as a silicone elastomer.

Some examples of biodegradable materials such as used in the flow-control plug 16 of FIG. 1 include, but are not limited to, synthetic polymers such as polyglycolic acid, and the copolymerization of lactide and glycolide. In addition, certain protein-based materials such as fibrin, collagen and certain tissue meshes, would be included in the materials that would biodegrade in contact with tissue elements.

Examples of the nontubular elements of FIGS. 9 through 16, would be materials that were non-biodegradable and would include, but would not be limited to, polystyrene, tetrachloroethylene, polyester, chloropropylene, substituted and unsubstituted polyolefins, polyvinyl chloride, polyvinylfluoride, trans-1,4 polyisoprene, and polymethylmethacrylate. These represent some of the non-biodegradable materials, but are not totally inclusive. Photon or heat or other energy-sensitive materials, can be categorized as consisting of compounds of substances such as polyesters, polyethylenes, polypropylene, tetrachloroethylene, chloropropylene, polymethylmethacrylate, and trans-1,4 polyisoprene. These materials are not only sensitive to the absorption of energy, but are considered to be biocompatible with tissue implantation.

The tubular element 31 can be any biocompatible, inert substance that is pliable, flexible, and resilient. Silicone rubber and thin-walled Teflon are examples of such materials, but not limited to these substances.

Photon, heat, or other energy absorbing compounds (dyes or chromophores) include, but are not limited to, sodium fluorescein, Q-Switched II, Rose Bengal, sulphan blue, Indocyanine Green (ICG), India Ink, patent plue, methylene blue, Sudan III, Toluidine blue, Sudan Black and Thionine.

What is claimed is;

1. An aqueous-drainage device for surgical implantation for the relief of aqueous fluid and intraocular pressure in a glaucomatous eye, comprising tubular means with longitudinally spaced retaining formations for retaining engagement to inner and outer limits of a local surgical bore to the anterior chamber of the eye and through a scleral part of the eye, and flow-restricting means associated with said tubular means and operative for at least a predetermined initial period of fluid exposure to substantially reduce the capacity of said tubular means to accommodate fluid flow, said flow-restricting means including a plug of liquid-absorbing material that is porous to the extent of permitting a substantially lesser flow than would be permitted by the tubular bore of said device in the absence of said plug, and a flexible filamentary element connected at one end to said plug, said filamentary element extending through said tubular means and beyond the open outer-limit end thereof.

2. An aqueous-drainage device for surgical implantation for the relief of aqueous fluid and intraocular pressure in a glaucomatous eye, comprising tubular means with longitudinally spaced retaining formations for retaining engagement to inner and outer limits of a local surgical bore to the anterior chamber of the eye and through a scleral part of the eye, and flow-restricting means associated with said tubular means and operative for at least a predetermined initial period of fluid exposure to substantially reduce the capacity of said tubular means to accommodate fluid flow, at least the outer-limit end of said tubular means being flexible, and said flow-restricting means being a clamp squeezing said flexible end and establishing a substantially reduced initial aqueous-flow capacity of said device, said clamp including a deformable element in squeezing confinement of said flexible end.

3. The device of claim 2, in which said deformable element is of shrinkable material that is shrinkable in response to an applied irradiation, whereby upon shrinkage of said material, the aqueous-flow capacity of said tubular means will increase.

4. An aqueous-drainage device for surgical implantation for the relief of aqueous fluid and intraocular pressure in a glaucomatous eye, comprising tubular means with longitudinally spaced retaining formations for retaining engagement to inner and outer limits of a local surgical bore to the anterior chamber of the eye and through a scleral part of the eye, the outer end of said tubular means being flexible, and flow-restricting means including a clamp squeezing and flexible end and establishing a substantially reduced initial aqueous-flow capacity of said device, said clamp including a deformable element in squeezing confinement of said flexible end, said deformable element being of a biologically inert material that is soluble in response to body-fluid exposure, whereby upon implantation and resultant exposure to body fluid, the aqueous flow capacity of said tubular means will increase.

5. The method of establishing controlled drainage of aqueous-humor fluid and relief of intraocular pressure in a glaucomatous eye, comprising the steps of surgically preparing a drainage hole through tissues of the cornea and adjacent sclera with the hole extending on a generally radially inward alignment between subconjunctival space and a corner of the anterior chamber; and thereafter transiently and compliantly dilating tissues around the hole, in the course of insertionally implanting in the hole a cylindrical tube selected for spaced radially outward retaining-flange formations one of which is at the inserted end of the tube, wherein the cylindrical outer diameter is sized to fit the drilled-hole diameter and wherein the spacing between the inner and outer flange formations accords substantially with the axial extent of the drilled hole and wherein the bore of the cylindrical tube has a temporary flow restriction that is operative for at least a predeterminable initial period of fluid exposure to substantially restrict what would otherwise by the capacity of the tube to accommodate fluid flow.

6. The method of claim 5, wherein the material of the flow restriction is selected for its properties of being biologically inert and soluble in response to the body-fluid exposure.

7. The method of claim 5, wherein the flow restriction is selected for its property of dimensional response to incident radiation, and the further step of selectively exposing the flow restriction to such radiation whereby to selectively control the drainage-flow rate through the fitted tube.

8. An aqueous-drainage device for surgical implantation for the relief of aqueous-humor fluid and intraocular pressure in a glaucomatous eye, comprising tubular means with two longitudinally spaced radially outward retaining formations for retaining engagement to inner and outer limits of a local surgical bore to the anterior chamber of the eye and through a scleral part of the eye, one of said retaining formations being at the inner end of said tubular means and the other end of said tubular means extending outwardly beyond the other of said retaining formations, and flow-restricting means associated with said other end and operative for at least a predetermined initial period of fluid exposure to substantially reduce the capacity of said tubular means to accommodate fluid flow.

9. The device of claim 8, in which said flow-restricting means is a soluble plug of bio-compatible material.

10. The device of claim 8, wherein said tubular means is cylindrically annular, and said retaining means comprises axially spaced radially outward flange formations.

11. The device of claim 10, in which at least the inner-limit flange has a frusto-conical outer surface which tapers radially inwardly in the axial direction away from the outer-limit flange.

12. The device of claim 10, in which said flow-restricting means is a clamp squeezing said flexible end and establishing a substantially reduced initial aqueous-flow capacity of said device, said clamp including a deformable element in squeezing confinement of said flexible end.

13. The device of claim 12, in which said deformable element is of shrinkable material that is shrinkable in response to an applied irradiation, whereby upon shrinkage of said material, the aqueous-flow capacity of said tubular means will increase.

14. The device of claim 12, in which said deformable element is of a biologically inert material that is soluble in response to body-fluid exposure, whereby upon implantation and resultant exposure to body fluid, the aqueous-flow capacity of said tubular means will increase.

15. The device of claim 12, in which said deformable element comprises a first member that is shrinkable in response to an applied irradiation of a first wavelength, and a second member that is expandable in response to an applied irradiation of a second and different wavelength, whereby the aqueous-flow capacity of said tubular means may be selectively controlled via selective irradiation of one or the other of said wavelengths.

16. The device of claim 8, wherein the material of said tubular means is a silicone elastomer.

17. An aqueous-drainage device for surgical implantation for the relief of aqueous-humor fluid and intraocular pressure in a glaucomatous eye, comprising tubular means with two longitudinally spaced radially outward retaining formations for retaining engagement to inner and outer limits of a local surgical bore to the anterior chamber of the eye and through a scleral part of the eye, one of said retaining formations being at the inner end of said tubular means and the other end of said tubular means extending outwardly beyond the other of said retaining formations, and flow-restricting means associated with said other end, said flow-restricting means being selectively controllable to vary the capacity of said tubular means to accommodate fluid flow.

* * * * *